US009179856B2

(12) United States Patent
Caduff et al.

(10) Patent No.: US 9,179,856 B2
(45) Date of Patent: Nov. 10, 2015

(54) SENSING DEVICE FOR BODY TISSUE PROPERTIES

(75) Inventors: Andreas Caduff, Zürich (CH); Mark Stuart Talary, Zürich (CH); Hans-Joachim Krebs, Lachen (CH); Alexander Megej, Zürich (CH); Francois Dewarrat, Zürich (CH)

(73) Assignee: BIOVOTION AG, Zurich (CH)

( * ) Notice: Subject to any disclaimer, the term of this patent is extended or adjusted under 35 U.S.C. 154(b) by 1000 days.

(21) Appl. No.: 13/264,774

(22) PCT Filed: Apr. 17, 2009

(86) PCT No.: PCT/CH2009/000121
§ 371 (c)(1),
(2), (4) Date: Dec. 28, 2011

(87) PCT Pub. No.: WO2010/118537
PCT Pub. Date: Oct. 21, 2010

(65) Prior Publication Data
US 2012/0095307 A1 Apr. 19, 2012

(51) Int. Cl.
*A61B 5/00* (2006.01)
*A61B 5/053* (2006.01)
(Continued)

(52) U.S. Cl.
CPC ........... *A61B 5/0531* (2013.01); *A61B 5/14532* (2013.01); *A61B 5/6828* (2013.01); *A61B 5/0261* (2013.01); *A61B 5/6824* (2013.01)

(58) Field of Classification Search
CPC .... A61B 5/0531; A61B 5/681; A61B 5/1455; A61B 5/14532

USPC .......................................... 600/345, 347, 365
See application file for complete search history.

(56) References Cited

U.S. PATENT DOCUMENTS

| 4,020,803 A   | 5/1977 | Thuren et al. |
| 4,450,064 A * | 5/1984 | Harman, III .................. 204/412 |

(Continued)

FOREIGN PATENT DOCUMENTS

| DE | 10 2006 010 653 A1 | 9/2007 |
| WO | 93/18395 A1 | 9/1993 |

(Continued)

OTHER PUBLICATIONS

International Search Report dated Oct. 23, 2009 and an International Preliminary Report on Patentability dated Oct. 27, 2011 for Application No. PCT/CH2009/000121.

(Continued)

*Primary Examiner* — Michael D'Angelo
*Assistant Examiner* — Christian Jang
(74) *Attorney, Agent, or Firm* — Ladas & Parry LLP

(57) ABSTRACT

A device is described for measuring a parameter of living tissue, in particular a glucose level, which parameter affects a response of said tissue to an electric field. The device comprises a substrate (2), which carries a ground electrode (10) as well as a plurality of signal electrodes (12a, 12b, 13a-13c, 14). The gaps (15) between the ground electrode and the signal electrodes are filled with a solid filler material (16) in order to provide an even surface. Optical reflection detectors (23a, 23b, 23c) can also be located in these gaps in order to avoid field distortions and obtain a compact design. The backside of substrate (2) carries electronic high-frequency components for improving signal quality.

20 Claims, 3 Drawing Sheets

(51) Int. Cl.
*A61B 5/145* (2006.01)
*A61B 5/026* (2006.01)

(56) References Cited

U.S. PATENT DOCUMENTS

| | | | |
|---|---|---|---|
| 4,509,531 | A | 4/1985 | Ward |
| 5,109,861 | A * | 5/1992 | Walinsky et al. ............ 600/463 |
| 5,353,802 | A | 10/1994 | Ollmar |
| 5,508,203 | A | 4/1996 | Fuller et al. |
| 5,701,902 | A | 12/1997 | Vari et al. |
| 5,758,644 | A | 6/1998 | Diab et al. |
| 5,792,668 | A | 8/1998 | Fuller et al. |
| 5,890,489 | A | 4/1999 | Elden |
| 6,070,092 | A | 5/2000 | Kazama et al. |
| 6,175,752 | B1 | 1/2001 | Say et al. |
| 6,442,408 | B1 | 8/2002 | Wenzel et al. |
| 6,487,906 | B1 | 12/2002 | Hock |
| 6,517,482 | B1 | 2/2003 | Elden et al. |
| 6,565,509 | B1 | 5/2003 | Say et al. |
| 6,762,609 | B2 | 7/2004 | Alanen et al. |
| 6,849,046 | B1 | 2/2005 | Eyal-Bickels et al. |
| 6,954,662 | B2 | 10/2005 | Freger et al. |
| 6,995,572 | B2 | 2/2006 | Arndt et al. |
| 7,693,561 | B2 | 4/2010 | Schrepfer et al. |
| 2002/0091384 | A1 * | 7/2002 | Hooven et al. ................ 606/41 |
| 2003/0214311 | A1 | 11/2003 | Alanen et al. |
| 2003/0216663 | A1 | 11/2003 | Jersey-Wlluhn et al. |
| 2004/0147819 | A1 | 7/2004 | Caduff et al. |
| 2005/0083992 | A1 | 4/2005 | Pesach |
| 2005/0203363 | A1 * | 9/2005 | Caduff et al. ................ 600/365 |
| 2006/0025664 | A1 | 2/2006 | Kim et al. |
| 2007/0161881 | A1 | 7/2007 | Ollmar et al. |
| 2007/0282180 | A1 | 12/2007 | Caduff et al. |
| 2008/0057526 | A1 | 3/2008 | Caduff et al. |
| 2008/0082004 | A1 | 4/2008 | Banet et al. |
| 2009/0312615 | A1 | 12/2009 | Caduff et al. |
| 2010/0004517 | A1 | 1/2010 | Bryenton et al. |
| 2010/0099960 | A1 | 4/2010 | Caduff et al. |
| 2010/0130883 | A1 | 5/2010 | Carpenter et al. |
| 2010/0298680 | A1 | 11/2010 | Talary et al. |
| 2011/0144525 | A1 | 6/2011 | Megej et al. |
| 2011/0160554 | A1 | 6/2011 | Megej et al. |
| 2011/0174288 | A1 | 7/2011 | Hanaoka et al. |

FOREIGN PATENT DOCUMENTS

| | | |
|---|---|---|
| WO | 01/26538 A1 | 4/2001 |
| WO | 02/069791 A1 | 9/2002 |
| WO | 2004/023125 A2 | 3/2004 |
| WO | 2005/053523 A1 | 6/2005 |
| WO | 2005/120332 A1 | 12/2005 |
| WO | 2007/053963 A1 | 5/2007 |
| WO | WO 2007053963 A1 * | 5/2007 |

OTHER PUBLICATIONS

M. Brischwein et al., Functional cellular assays with multiparametric silicon sensor chips, The Royal Society of Chemistry 2003, Lab Chip, 2003, 3, 234-240.

S. Gawad et al., Micromachined impedance spectroscopy flow cytometer for cell analysis and particle sizing, The Royal Society of Chemistry 2001, Lab on a Chip, 2001, 1, 76-82.

A. Caduff et al., First human experiments with a novel non-invasive, non-optical continuous glucose monitoring system, Biosensor and Bioelectronics 19 (2003), 209-217.

Andreas Caduff et . al., Non-invasive glucose monitoring in patients with Type 1 diabetes: A Multisensor system combining sensor for dielectric and optical characterization of skin, Biosensor and Bioelectronics 24 (2009), 2778-2784.

Esko Alanen at aI., Penetration of electromagnetic fields of an open-ended coaxial probe between I MHz and 1 GHz in dielectric skin measurements, N169-N176.

F. Dewarrat et aI., Measurement and Simulation of Conductive Dielectric Two-layer Materials with a Multiple Electrodes Sensor, 1070-9878/08/$25.00 © 2008 IEEE, 1406-1414.

B.C. Lesieutre et aI., Forward and Inverse Parameter Estimation Algorithms of Interdigital Dielectrometry Sensors, IEEE Transactions on Dielectrics and Electrical Insulation vol. 8 No. 4, Aug. 2001, 577-588.

M.S. Talary, et aI., An RCL Sensor for Measuring Dielectrically Lossy Materials in the MHz Frequency Range, IEEE Transactions on Dielectrics and Electrical Insulation vol. 13, No. 2; Apr. 2006, 247-256.

Daniel Huber et aI., The compensation of perturbing temperature fluctuation in glucose monitoring technologies based on impedance spectroscopy, Med Bio Eng Comput (2007) 45, 863-876.

Mark S. Talary et aI., In vivo life sign application of dielectric spectroscopy and noninvasive glucose monitoring, Elservier Journal of Non-Crystalline Solids 353 (2007), 4515-4517.

A.H. Lackermeier et aI., In Vivo ac Impedance Spectroscopy of Human Skin, XP008029774, 197-213.

S.S. Stuchly and C.E. Bassey, Microwave coplanar sensors for dielectric measurements, Meas. Sci. Technol. 9 (1998), 1324-1329.

A. Kraszewski et aI., Dielectric properties and a model of biphase water suspension at 9.4 GHz, Journal of Applied Physics, vol. 47, No. 4, Apr. 1976, 1275-1277.

Jorgen Serup et aI., Handbook of Non-Invasive Methods and the Skin, Second Edition, Published in 2006 by CRC Press Taylor & Francis Group, ISBN-10: 0-8493-1437-2, 665-671.

Hanli Liu et aI., Determination of optical properties and blood oxygenation in tissue using continuous NIR light, Phys. Med. Biol. 40 (1995), 1983-1993.

Omar S. Khalil, Ph.D. Non-Invasive Glucose Measurement Technologies: An Update from 1999 to the Dawn of the New Millenium, Diabetes Technology & Therape Utics, vol. 6, No. 5, 2004, 660-695.

P. Linderholm et aI., Analytical expression for electric field between two facing strip electrodes in microchannel, Electronics Letters Feb. 2, 2006 vol. 42 No. 3, 2 pages.

Jussi Tenhunen et aI., Non-invasive glucose measurement based on selective near infrared absorption; requirements on instrumentation and spectral range, Measurement 24 (1998), 173-177.

Andreas Caduff et. aI., Multisensor Concept for non-IllvaSIVe Physiological Monitoring, Instrumentation and Measurement Technology Conference—IMTC 2007 Warsaw, Poland, May 1-3, 2007, 1-4.

Cheng P. Wen , Coplanar Waveguide: A Surface Strip Transmission Line Suitable for Nomeciprocal Gyromagnetic Device Applications, IEEE Transactions on Microwave Theory and Techniques, vol. MTT-17, No. 12, Dec. 1969, 1087-1090.

Sanghyun Seo et aI., High Frequency Wideband Permittivity Measurements of Biological Substances Using Coplanar Waveguides and Application to Cell Suspensions, 978-1-4244-1780-3/08/$25.00 © 2008 IEEE, 915-918.

A. Raj et aI., Wide Bandwidth Measurement of Complex Permittivity of Liquids Using Coplanar Lines, IEEE Transactions on Instrumentation and Measurement, vol. 50, No. 4, Aug. 2001, 905-909.

Office Action dated Sep. 17, 2012 for Application No. EP 09 775 716.5-1265.

* cited by examiner

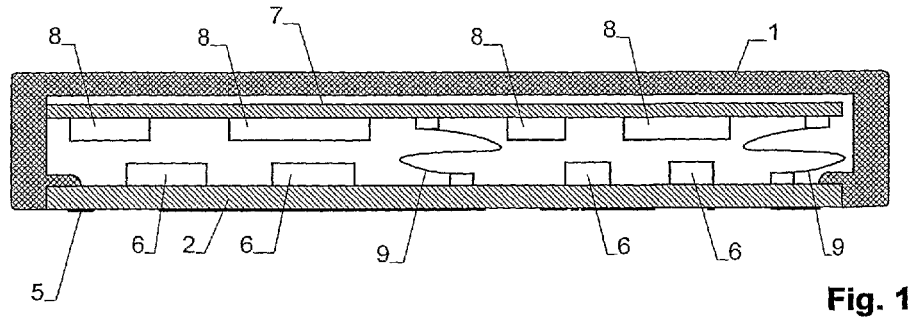
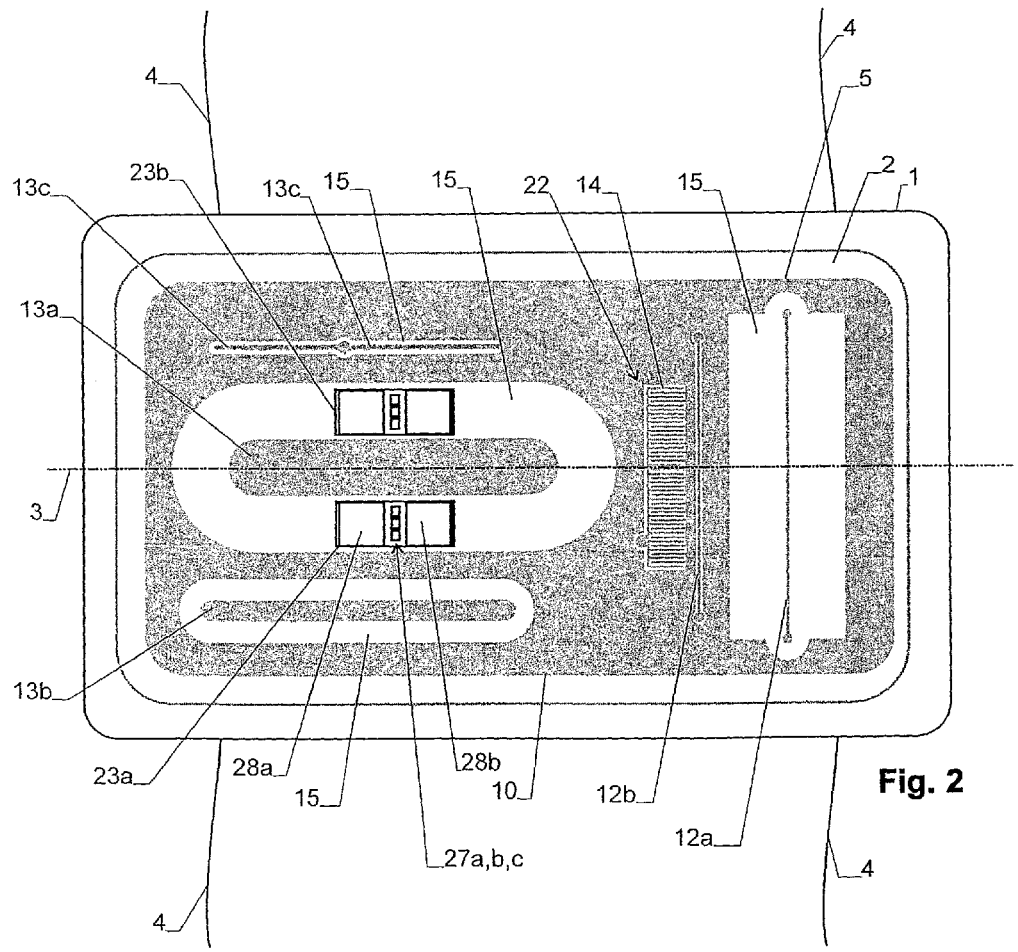

SENSING DEVICE FOR BODY TISSUE PROPERTIES

TECHNICAL FIELD

The invention relates to a device for measuring a parameter of living tissue, in particular a glucose level, which parameter affects a response of said tissue to an electric field.

BACKGROUND ART

WO 02/069791 describes a device for determining a parameter of living tissue. The device comprises an electrode arrangement mounted to a substrate, as well as a control unit adapted to determine the response of the tissue to the electric field generated by the electrodes. This type of device exploits the fact that various parameters of living tissue affect the dielectric response of the same. For example, this type of device allows to measure glucose level, as described in WO 02/069791, as well as the water concentration in the skin.

Devices of this type can provide better results if they comprise sensors for other types of parameters. For example, WO 2007/053963 describes an improved device that not only measures the response to the field applied by the electrodes, but further comprises temperature sensors as well as optical sensors for measuring a reflection or transmission of the tissue.

DISCLOSURE OF THE INVENTION

It is a general object of the invention to design the electrodes of a sensor of this type, and in particular the mechanical setup of the electrode arrangement.

This object is achieved by the sensor of claim 1. Accordingly, the electrode arrangement comprises at least two electrodes mounted to a first side of a substrate. The electrodes are separated by a gap. The gap, which has non-zero volume due to the finite thickness of the electrodes, is filled at least partially with a solid. In contrast to prior art, where the gap is not filled and therefore the surface of the electrode arrangement facing and normally in contact with the skin is not planar, filling the gap with a solid allows to form a substantially flat surface. This allows to reduce pressure induced vasodilation at the electrode edges and underlying tissue, and helps to avoid irritations induced by friction at the electrode edges, which in turn allows more reliable measurements even under long-term application. Additionally and importantly, this prevents the accumulation of the sweat in these gaps.

In an advantageous embodiment, the gap between the electrodes is used to receive at least part of an optical reflection sensor. Locating the optical reflection sensor, as it can e.g. be used for perfusion measurements, at this location has two advantages: On the one hand, it allows to carry out the optical measurement at the same location and underlying tissue volume as the electrical measurement, thereby allowing a better correlation between the two. On the other hand, its presence in the gap hardly affects the electric field distribution in the tissue, while placing the optical reflection sensor within an electrode would affect the field to a larger extent.

In another advantageous embodiment, the electrode arrangement comprises a ground electrode and several signal electrodes on the first side of the substrate. The signal electrodes are arranged in openings formed within the ground electrode, and the gaps mentioned above are formed between the respective inner edges of the openings and the outer edges of the signal electrodes.

Advantageously, the sensor comprises a first set of signal electrodes surrounded by gaps of different widths, such that electrical fields of different geometries are formed. The first set of signal electrodes are connected to a first signal generator operating at a frequency of at least 1 GHz. Similarly, a second set of signal electrodes surrounded by gaps of different widths is provided, with the second set of signal electrodes being connected to a second signal generator operating at a frequency between 0.1 and 500 MHz. This makes it possible to carry out two depth-resolved measurements at two important frequency ranges, with the electrode geometries optimized to the specific frequency ranges.

A shield electrode can be embedded within the substrate in order to shield the electronics on the second side of the substrate. This is particularly advantageous when measuring signals in the GHz range. In that case, the shield electrode should be located at a smaller distance from the first set of signal electrodes then from the second set of signal electrodes. This allows to form coplanar waveguides with the first set of signal electrodes in the GHz range. On the other hand, it prevents the shield electrode from grounding a large amount of the electrical field at the location of the second set of signal electrodes, thereby allowing to generate MHz fields that primarily are located within the tissue.

In yet another advantageous embodiment, the device comprises a first signal generator connected to at least one of the electrodes and generating a signal with a frequency of at least 1 GHz as well as a first signal detector for detecting this signal, e.g. after it has been transmitted through the electrode. Both, the signal generator and a signal detector, are mounted to (i.e. attached to and electrically connected to) the second side of the substrate, i.e. to the side opposite the electrodes. This allows to create short and well-defined signal paths between electrodes and electronics.

BRIEF DESCRIPTION OF THE DRAWINGS

The invention will be better understood and objects other than those set forth above will become apparent when consideration is given to the following den tailed description thereof. Such description makes reference to the annexed drawings, wherein:

FIG. 1 shows a sectional view of a device,

FIG. 2 shows a bottom view of the device of FIG. 1,

MODES FOR CARRYING OUT THE INVENTION

General Design

Figure 3:
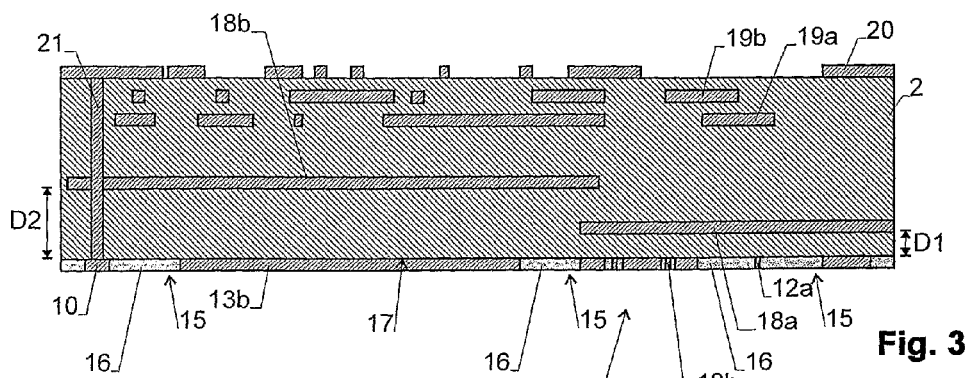
FIG. 3 is a more detailed sectional view of the substrate parallel to its longitudinal axis 3.

The general design of an advantageous embodiment of the device is shown in FIGS. 1 and 2. The device comprises a housing 1, e.g. of plastics. One side of the device, in the following called the "bottom side", is closed by a substrate 2. Substrate 2 is rectangular and elongate and has a longitudinal axis 3. A band or wristband 4 is attached to housing 1, extends perpendicular to longitudinal axis 3 and allows to mount the device e.g. to an arm or leg of a person, with longitudinal axis 3 extending parallel to the longitudinal axis of the arm or leg.

At a first side (bottom side) substrate 2 carries a plurality of electrodes formed by a structured metal layer 5. Metal layer 5 is shown in gray in FIG. 2. The design of the electrodes is described in more detail below. On its second side (top side) electronic components 6 are mounted to substrate 2 and connected to metal leads on the surface or within substrate 2.

Housing 1 encloses at least one printed circuit 7 in addition to substrate 2, which carries further electronic components 8. Electrical connectors 9 are provided for connecting printed circuit board 7 to substrate 2.

In addition, the device typically also contains a battery as well as interface and/or display components (not shown).

Substrate Design

One of the key components of the device is substrate 2 and its design, which can be best seen from FIGS. 2 and 3. It must be noted that the sectional view of FIG. 3 is zoomed along its vertical direction in order to improve the visibility of the various layers of the substrate.

As mentioned, substrate 2 has a first (bottom) side and a second (top) side, with the first side being applied to a person's skin during operation of the device.

Advantageously, the metal layer 5 is formed by a copper and a gold layer, with the gold layer forming the surface of the electrodes. The gold layer is directly connected to the copper layer, in particular without an intermediate nickel containing layer in order to avoid allergic reactions. Advantageously, the metal layer is formed using "lamination chemical thickgold" technology. The gold layer should be non-porous and not comprise any pinholes in order to avoid dirt and sweat from entering the same that could lead to electrolysis at the electrodes.

Alternatively, or in addition thereto, metal layer 5 can be covered by a physiologically inert protective layer, but such a layer should be thin and uniform such that the electrodes can be placed as close to the skin as possible.

Metal layer 5 is structured to form a ground electrode 10 having openings. Signal electrodes 12a, 12b, 13a, 13b, 13c and 14 are placed within these openings, such that gaps 15 are formed between the inner edges of the openings and the outer edges of the signal electrodes. Each signal electrode 12a, 12b, 13a, 13b, 13c and 14 is completely surrounded by such a gap 15.

As can be seen in FIG. 3, the gaps 15 are filled with a solid filler material 16. Filler material 16 is a dielectric, i.e. non-conductive material, e.g. glass. It is of an advantage if this material possesses the same dielectric parameters—especially the permittivity—as the substrate 2.

In the embodiment of FIG. 3, substrate 2 has a flat surface 17 on its first side, and the electrodes are mounted to the top of this surface, such that, without the filler material 16, the gaps 15 would form trenches or recesses in the bottom side of the device, which would lead to skin irritation as well as providing regions for dirt and sweat accumulation.

As can further be seen from FIG. 3, a shield electrode 18a, 18b is embedded within substrate 2. The primary purpose of shield electrode 18a, 18b is to shield the electronics within the device from high frequency electromagnetic radiation and to form a defined ground.

As can be seen, the shield electrode comprises two sections 18a, 18b embedded at different depths within substrate 2. Section 18a is adjacent to the signal electrodes 12a, 12b of the first set, while section 18b is adjacent to the signal electrodes 13, 13b, 13c of the second set. The distance D1 between the shield electrode in section 18a and the signal electrodes 12a, 12b is smaller than the distance D2 between the shield electrode in section 18b and the signal electrodes 13a, 13b, 13c. Typically, D1 should be smaller than 1 mm, e.g. 0.5 mm, while D2 should be at least 1.5 mm (for a typical dielectric constant of the substrate material of 3.5-4.0 at frequencies around 1 GHz). The reasons for these different distances are:

a) As described below, the first set of signal electrodes 12a, 12b are operated as "coplanar waveguides" (CPW) at frequencies of at least 1 GHz. By placing section 18a of the shield electrode sufficiently close to the signal electrodes 12a, 12b, it becomes possible to operate the waveguide as a "conductor-backed coplanar waveguide" with well defined electric field geometry and electromagnetic-field distribution.

b) Also as described below, the second set of signal electrodes 13a, 13b, 13c are operated as capacitive sensors in the MHz-range. At these frequencies, a shield electrode too close to the signal electrodes would "ground" a large amount of the electrical field, thereby reducing the strength and reach of the field into the body.

Advantageously, shield electrode 18a, 18b is connected to ground, i.e. to the same potential as ground electrode 10.

As can also be seen in FIG. 3, substrate 2 comprises further embedded, structured metal layers 19a, 19b on the second (top) side of shield electrode 18a as well as a structured top layer 20 on the surface at the second side of substrate 2, which together form electrical leads of the printed circuit carrying the electronic components 6.

To interconnect the various metal layers shown in FIG. 3 as appropriate, vias or lead-throughs 21 extend through substrate 1. Advantageously the vias 21 are mechanically closed, i.e. they do not form mechanical openings within substrate 2. Advantageously, so-called "buried vias" are used.

Electrode Geometries

As can be seen from FIG. 2, the signal electrodes 12a, 12b and 13a, 13b, 13c of the first and second set are straight strip electrodes located in the center of respective elongate openings of ground electrode 10. Signal electrode 14, on the other hand, forms, together with ground electrode 10, a set of interdigital electrodes 22. In the following, we discuss the three sets of signal electrodes in more detail.

a) First Set of Signal Electrodes (GHz)

The first set of signal electrodes 12a, 12b is operated, as mentioned, at a frequency of at least 1 GHz, with each signal electrode forming a conductor-backed coplanar waveguide together with the surrounding part of ground electrode 10 and shield electrode 18a. The signal from the signal generator is fed to a first end of the signal electrode and the signal at the second, opposite end is fed to a signal detector, which will be described below.

As described in WO 2005/120332 and WO 2007/053963, it is advantageous to generate electric fields reaching into different depths of the tissue, for which purpose the width of the gaps around the signal electrodes 12a and 12b differ. Advantageously: for signal electrode 12a, the width of the gap is typically up to 4 mm, for signal electrode 12b the width of the gap is typically up to 0.15 mm. Both signal electrodes 12a, 12b have a width of 0.2 mm or less and a length of 20-23 mm.

The signal electrodes 12a, 12b of the first set are parallel to each other and extend perpendicularly to longitudinal axis 3. It has been found that for high-frequency sensors of this type, an arrangement perpendicular to the arm/leg of the wearer provides more robust measurements that are less prone to signal errors due to mechanical shifts related to sensor contact with the skin. However, the signal electrodes 12a, 12b may also extend parallel to longitudinal axis 3.

b) Second Set of Signal Electrodes (MHz)

The second set of signal electrodes 13a, 13b, 13c is operated at a frequency between 0.1 and 500 MHz. Each signal electrode 13a, 13b, 13c is strip-shaped. The signal from the signal generator is fed to a contact point in the center of the signal electrode, and a signal depending on the impedance between the signal electrode and the ground electrode is measured, as e.g. described in WO 2007/053963 or WO 2005/053523.

Again, differing geometries are used in order to generate electric fields reaching into different depths of the tissue. Hence, the widths of the gaps 15 around the signal electrodes 13a, 13b, 13c differ. Advantageously: for signal electrode 13a, the width of the gap as well as the width of the signal electrode are typically 4 mm, for signal electrode 13b the width of the gap as well as the width of the signal electrode are typically 1.5 mm, and for signal electrode 13b the width of the gap as well as the width of the signal electrode are typically 0.3 mm. The length of the signal electrodes 13a, 13b, 13c should be as large as possible in order to have a large measured volume of skin and underlying tissue.

The signal electrodes 13a, 13b, 13c extend parallel to each other and parallel to the longitudinal axis 3, which increases the interaction length between the electrodes and the tissue within the wearer's arm or leg.

c) Interdigital Electrodes (kHz)

The interdigital electrodes 22 are operated at a frequency below 200 kHz, in particular at 1 kHz. Their primary purpose is the measurement of sweat and moisture, as described in section 2.2 of WO 2007/053963. The signal from the signal generator is fed to a contact point in the center of signal electrode 14, and a signal depending on the impedance between the signal electrode and the ground electrode is measured, as described in WO 2007/053963.

The width of the fingers of the interdigital electrodes as well their mutual distance is advantageously in the order of 0.15 mm.

Optical Sensors

As described in WO 2007/053963, it is advantageous to combine the electrical measurements with optical measurements, in particular optical reflectance measurements. For this purpose, the device can be equipped with at least one optical reflection sensor. Such a sensor allows to obtain a measure of the perfusion of the tissue.

In the embodiment of FIG. 2, the device comprises two such optical reflection sensors 23a and 23b. Each optical reflection sensor 23a, 23b is arranged in the gap around signal electrode 13a.

As mentioned above, arranging the optical reflection sensor in the gap around an electrode has various advantages, in particular because it allows an optical measurement at the same location as the electrical measurement, and field distortions caused by the sensor are small.

Figure 4:
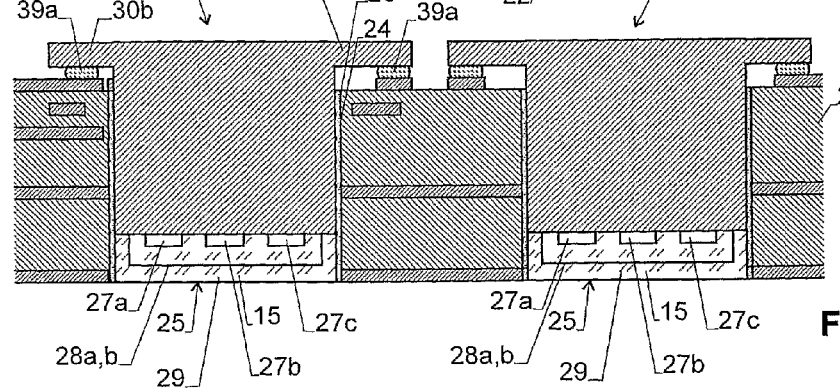
FIG. 4 is a sectional view of the substrate at the location of the wide-gap MHz-electrode and its adjacent two optical reflection sensors.

Advantageously, and as shown in FIG. 4, each optical reflection sensor extends through an opening 24 in substrate 2 and is fixed in place therein, e.g. by gluing or soldering. Opening 24 ends in gap 15 between signal electrode 13a and ground electrode 10.

At the first (bottom) side of the device, the surface 25 of the optical reflection sensor 23a, 23b is flush with the surface of the electrodes. Any gap 26 surrounding optical reflection sensors 23a, 23b should be filled, at least close to the surface of substrate 2, with a filler material for blocking the entry of moisture and dirt.

At its rear end (i.e. at the end facing away from the first (bottom) side of the device, the optical reflection sensors 23a, 23b can e.g. be directly connected to the circuitry at the second side of substrate 2 by means of solder bumps 39a. For this purpose, each of the optical reflection sensors 23a, 23b comprises a base 39b which laterally extends beyond the rim of opening 24 and carries the contacts to be soldered to the pumps 39a.

Each optical reflection sensor 23a, 23b advantageously comprises at least one light source and at least one light detector. In the embodiment shown in FIGS. 2 and 4, each optical reflection sensor comprises three light sources 27a, 27b, 27c arranged in a row that extends perpendicularly to the longitudinal axis of the sensor. The light sources 27a, 27b, 27c advantageously emit light in the visible or near-infrared spectral range. Furthermore, in the embodiment of FIGS. 2 and 4, each optical reflection sensor comprises two light detectors 28a, 28b, with the light sources 27a, 27b, 27c located between the light detectors 28a, 28b, such that the light detectors 28a, 28b are able to sense light scattered in forward as well as backward direction respectively to the longitudinal axis of the sensor but having different separations to the light sources 27a, 27b and 27c allowing for perfusion at different depths in the tissue to be measured.

The light sources 27a, 27b, 27c as well as the light detectors 28a, 28b are covered by a window 29, which is located at least partially in gap 15. Window 29 is transparent for light as emitted by the light sources 27a, 27b, 27c.

To keep a distortion of the electric field caused by the optical reflection sensors minimal, the optical reflection sensors 23a, 23b should have dielectric properties close to those of substrate 2.

Using at least two light sources with different optical emission spectra has the advantage that differing tissue processes giving rise to a spectrally differing reflectance changes can be distinguished.

In particular, if two light sources are used, one should generate a wavelength below 600 nm and the other a wavelength above 700 nm, advantageously at approximately 568 nm and 800 nm. If three light sources are used, the first one should advantageously generate light at a wavelength below 600 nm, the second one light of a wavelength above 700 nm, and the third one light at a wavelength between 600 and 700 nm. Advantageous values were found to be 568 nm, 800 nm and 660 nm, respectively. It must be noted that 568 nm and 800 nm are "isosbestic" points where the haemoglobin absorption does not depend on the level of oxygenation. In order to correct for skin perfusion changes, the haemoglobin related signal can be calculated by the ratio of the absorption at 568 nm and 800 nm. The oxygen signal can be calculated at 660 nm, a wavelength where the difference between the absorbance of oxygenated and deoxygenated haemoglobin is at its largest, as a ratio to the 800 nm.

The spectral width of the light sources 23a, 23b and 23c should be smaller than 50 nm for sufficient spectral resolution, but it will typically be in the order of a few 5 to 10 nm, as it is typical for light-emitting diodes.

Figure 5:
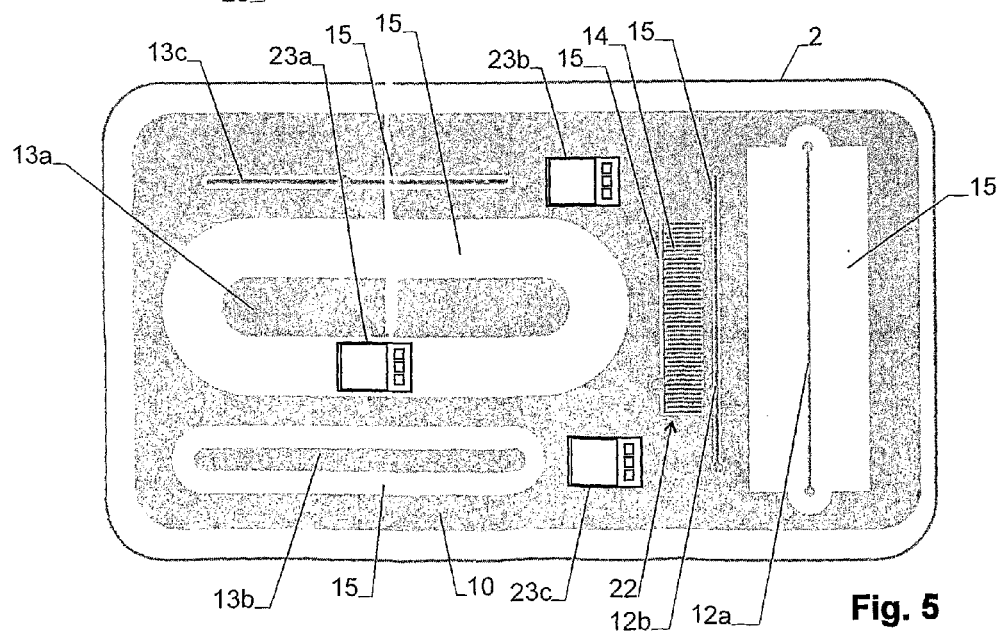
FIG. 5 is an alternative design of the substrate with other types of optical reflection sensors.

FIG. 5 shows an alternative embodiment of the device with three optical reflection sensors, only one of which is located in the gap 15 around an electrode, while the others are located in separate openings in the ground electrode 10. In contrast to the embodiment of FIG. 2, each optical reflection sensor 23a, 23b, 23c comprises a single light detector only, which allows a more compact design at a somewhat reduced sensitivity.

Electronics

Figure 6:
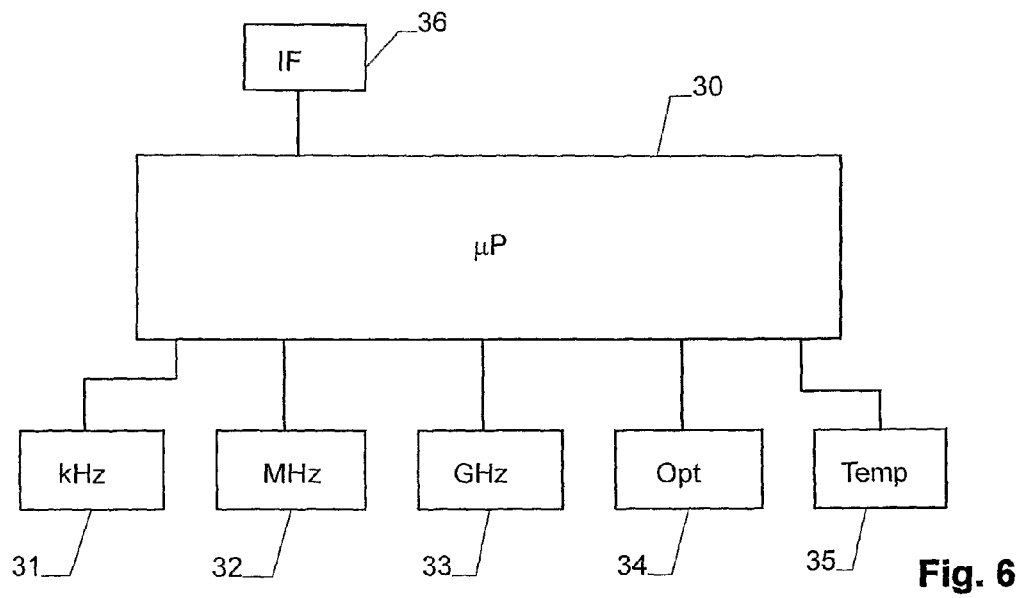
FIG. 6 is a block circuit diagram of the device.

FIG. 6 shows a block diagram of an embodiment of the device. It comprises a control unit 30, e.g. a microprocessor with program and data memory as known to the skilled person, which controls the operation of the device. It is connected to various sensors, in particular:

a) A low-frequency sensor 31 comprising a signal generator and signal detector in the frequency range below 200 kHz, which uses the interdigital electrodes 22 for its measurements.

b) A medium-frequency sensor 32 comprising a signal generator and signal detector in the frequency range between 0.1 MHz and 500 MHz, which uses the second set of signal electrodes 13a, 13b, 13c for its measurements.

c) A high-frequency sensor 33 comprising a signal generator and signal detector in the frequency range of at least 1 GHz, which uses the first set of signal electrodes 12a, 12b for its measurements.

d) An optical detector 34 measuring optical reflection by means of the optical reflection sensors 23a, 23b, 23c.

e) A temperature sensor 35 measuring a temperature of the surface of the tissue as well as the temperature within housing 1, e.g. by means of a first temperature sensing device in direct thermal contact with substrate 2, as well as by means of a second temperature sensing device arranged inside housing 1.

In addition to the sensors, control unit 30 controls an interface 36, such as a USB- or Bluetooth-Interface, for exchanging data with an external device, with an external device which is used for analyzing and displaying the data measured by the present device. It must be noted, though, that this type of functionality can also be incorporated into the present device itself.

Figure 7:
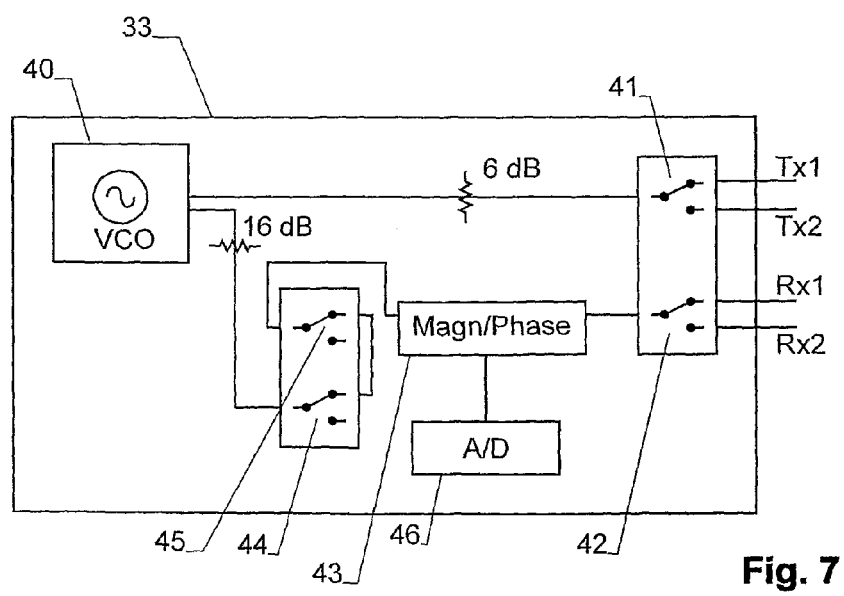
FIG. 7 is a block circuit diagram of the GHz-electronics of the device.

FIG. 7 shows a more detailed diagram of the high-frequency sensor 33. It comprises a voltage-controlled oscillator 40 with two identical outputs. One of the outputs is connected to a first switch 41, from where it is selectively sent to the input end Tx1, Tx2 of one of the signal electrodes 12a, 12b. The appropriate one of the signals Rx1, Rx2 from the output ends of the signal electrodes 12a, 12b is selected with a second switch 42 and fed to a first input of a magnitude/phase detector 43. The other output of oscillator 40 is routed through two static switches 44, 45 of the same type as the switches 41, 42 and then to the second input of magnitude/phase detector 43. The purpose of the static switches 44, 45 is to increase the symmetry of the two signal paths from oscillator 40 to magnitude/phase detector 43 in terms of temperature and technological variations.

Magnitude/phase detector 43 measures the relative magnitude and phase of the signals at its two inputs and feeds the corresponding value to an A/D converter 46, from where it can be read by control unit 30.

The components of the high-frequency sensor shown in FIG. 7, at least the signal generator or oscillator 40 as well as the signal detector or magnitude/phase detector 43 are advantageously mounted to the second (top) side of said substrate 2, as mentioned above, in order to have short and well-defined signal paths for the high-frequency signals to and from the signal electrodes 12a, 12b. The oscillator 40 and the signal detector 43 (or its A/D-converter 46) are electrically connected to printed circuit board 7 by means of the connectors 9, where control unit 30 is located.

Operation

The principles of operation of this type of device has been described in WO 2007/053963 and need not be repeated here.

As described in WO 2007/053963, the device can be used for a measurement of the glucose level within the tissue. It must be noted, though, that the same type of device can also be used for measuring another parameter that affects a response of the tissue to an electric field, as e.g. described in WO 02/069791. In particular, the device can be used to measure skin hydration since the impedance of the signal electrodes in respect to ground is directly dependent on the concentration of water within the tissue. In that case, the optical reflection sensors can be used to distinguish between water concentration variations due to blood perfusion and water concentration variations due to sweat or lymphatic fluid.

The device can also be used for the determination of the complex dielectric parameters of a tissue. In particular, the skin dielectric parameters can be measured employing the described embodiment. A combination of the above mentioned parameters can be used for the description of different skin and body states as hydration and dehydration; normal and pathological moisturisation.

Further applications include the determination of advanced states associated with metabolic diseases, such as renal disturbances that lead to fluid imbalance in the tissue, and reduction in cardiac function leading to a disturbance of the skin microcirculation can also be preferably monitored.

While there are shown and described presently preferred embodiments of the invention, it is to be distinctly understood that the invention is not limited thereto but may be otherwise variously embodied and practiced within the scope of the following claims.

The invention claimed is:

1. A device for measuring a parameter of living tissue, which parameter affects a response of said tissue to an electric field, said device comprising
    a substrate (2),
    an electrode arrangement (10, 12a, 12b, 13a-13c, 14) comprising at least a first and a second electrode and being mounted on a first side of said substrate (2), wherein said first and second electrodes are separated by a gap (15),
    a control unit (30) adapted to determine the response of said tissue to the electric field generated by said electrodes,
    wherein said gap (15) is filled at least partially with a solid (16), and
    wherein said device further comprises at least one optical reflection sensor (23a-c), and wherein said at least one optical reflection sensor (23a-c) extends into said gap (15).

2. The device of claim 1, wherein said substrate (2) has a flat surface (17) on said first side and wherein said first and second electrodes are mounted on said flat surface (17).

3. The device of claim 1, wherein said optical reflection sensor (23a-c) extends into or through an opening (24) in said substrate (2), and wherein said opening (14) ends in said gap (15).

4. The device of claim 1, wherein said optical reflection sensor (23a-c) comprises at least one light source (27a, 27b, 27c) and at least one light detector (28a, 28b) covered by a transparent window (29), wherein said window (29) is located at least partially in said gap (15).

5. The device of claim 4, wherein said optical reflection sensor (23a-c) comprises two light detectors (28a, 28b), and wherein said at least one light source (27a, 27b, 27c) is located between said two light detectors.

6. The device of claim 5, wherein said optical reflection detector comprises a first light source (27a) generating light at a wavelength below 600 nm, a second light source (27b) generating light at a wavelength above 700 nm, and a third light source (27c) generating light at a wavelength between 600 and 700 nm.

7. The device of claim 4, wherein said optical reflection detector comprises a first light source (27a) generating light at a wavelength below 600 nm and a second light source (27b) generating light at a wavelength above 700 nm.

8. The device of claim 1, wherein said electrode arrangement (10, 12a, 12b, 13a-5 13c, 14) comprises a ground electrode (10) and several signal electrodes (12a, 12b, 13a-13c, 14) on said first side of said substrate (2), wherein said signal electrodes (12a, 12b, 13a-13c, 14) are arranged in openings of said ground electrode (10), and wherein said gaps (15) are formed between inner edges of said openings and outer edges of said signal electrodes (12a, 12b, 13a-13c, 14).

9. The device of claim 1, wherein the parameter is a glucose level.

10. A device for measuring a parameter of living tissue, which parameter affects a response of said tissue to an electric field, said device comprising
a substrate (2),
an electrode arrangement (10, 12a, 12b, 13a-13c, 14) comprising at least a first and a second electrode and being mounted on a first side of said substrate (2), wherein said first and second electrodes are separated by a gap (15),
a control unit (30) adapted to determine the response of said tissue to the electric field generated by said electrodes,
wherein said gap (15) is filled at least partially with a solid (16),
wherein said electrode arrangement (10, 12a, 12b, 13a-13c, 14) comprises a ground electrode (10) and several signal electrodes (12a, 12b, 13a-13c, 14) on said first side of said substrate (2), wherein said signal electrodes (12a, 12b, 13a-13c, 14) are arranged in openings of said ground electrode (10), and wherein said gaps (15) are formed between inner edges of said openings and outer edges of said signal electrodes (12a, 12b, 13a-13c, 14), said device further comprising
a first set (12a, 12b) of signal electrodes surrounded by gaps (15) of different widths,
a second set (13a-13c) of signal electrodes surrounded by gaps (15) of different widths,
a first signal generator (33) connected to said first set (12a, 12b) of signal electrodes and operating at a frequency of at least 1 GHz, and
a second signal generator (32) connected to said second set (13a-13c) of signal electrodes and operating at a frequency between 0.1 and 500 MHz.

11. The device of claim 10, wherein said first and second sets of signal electrodes are elongate strip electrodes, wherein the electrodes in each set extend parallel to each other and perpendicular to the electrodes of the other set,
and wherein said device comprises a band (4) for attaching said device on an arm or leg, wherein said band extends perpendicularly to an axis (3) of said device, wherein the signal electrodes of said first set (12a, 12b) extend perpendicularly to said axis (3) and/or the signal electrodes of said second set (13a-13c) extend parallel to said axis (3).

12. The device of claim 10, wherein said substrate (2) comprises a shield electrode (18a, 18b) embedded within said substrate (2), and wherein said shield electrode (18a, 18b) is electrically connected to said ground electrode.

13. The device of claim 10, wherein said shield electrode (18a, 18b) is at a first distance (D1) from said first set (12a, 12b) of signal electrodes and at a second distance (D2) from said second set (13a-13c) of signal electrodes, wherein said first distance (D1) is smaller than said second distance (D2), and wherein said first distance (D1) is smaller than 1 mm and said second distance (D2) is at least 1.5 mm.

14. The device of claim 10, wherein said interdigital electrodes (22) are arranged between said first and said second sets (12a, 12b; 13a-13c) of electrodes.

15. The device of claim 10, wherein the parameter is a glucose level.

16. A device for measuring a parameter of living tissue, which parameter affects a response of said tissue to an electric field, said device comprising
a substrate (2),
an electrode arrangement (10, 12a, 12b, 13a-13c, 14) comprising at least a first and a second electrode and being mounted on a first side of said substrate (2), wherein said first and second electrodes are separated by a gap (15), and
a control unit (30) adapted to determine the response of said tissue to the electric field generated by said electrodes,
wherein said gap (15) is filled at least partially with a solid (16),
wherein said electrode arrangement (10, 12a, 12b, 13a-13c, 14) comprises a ground electrode (10) and several signal electrodes (12a, 12b, 13a-13c, 14) on said first side of said substrate (2), wherein said signal electrodes (12a, 12b, 13a-13c, 14) are arranged in openings of said ground electrode (10), and wherein said gaps (15) are formed between inner edges of said openings and outer edges of said signal electrodes (12a, 12b, 13a-13c, 14),
said device further comprising at least one pair of electrodes designed as interdigital electrodes (22), and wherein said device further comprising a third signal generator (31) connected to said interdigital electrodes (22) and generating a signal at a frequency below 0.2 MHz.

17. The device of claim 16, further comprising a first signal generator (40) connected to at least one of said electrodes and generating a signal with a frequency of at least 1 GHz and a first signal detector (43) connected to at least one of said electrodes and detecting said signal of at least 1 GHz, wherein said first signal generator (40) and said first signal detector (43) are mounted to a second side of said substrate (2).

18. The device of claim 17, further comprising at least one printed circuit (7) in addition to said substrate (2), wherein said printed circuit (7) is electrically connected to said first signal detector (43) and said first signal generator (40).

19. The device of claim 18, wherein said electrodes comprise a copper layer and a gold layer, and wherein said gold layer forms a surface of said electrodes and is directly connected to said copper layer.

20. The device of claim 16, wherein the parameter is a glucose level.

* * * * *